United States Patent [19]

Chan

[11] 4,248,795
[45] Feb. 3, 1981

[54] PREPARATION OF ORGANIC SULFONE COMPOUNDS

[75] Inventor: John K. Chan, Charleston, W. Va.

[73] Assignee: Union Carbide Corporation, New York, N.Y.

[21] Appl. No.: 767,488

[22] Filed: Feb. 10, 1977

[51] Int. Cl.$^3$ ............................................ C07C 131/00
[52] U.S. Cl. ................................ 564/255; 260/465 E; 260/465.5 R; 564/265; 564/268; 568/28
[58] Field of Search ........ 260/566 AC, 566 A, 465 E, 260/465 SR, 453 RW, 558 S, 561 A, 607 AR, 607 AL, 607 E, 557 R; 560/12, 13

[56] References Cited

FOREIGN PATENT DOCUMENTS 2436817  2/1976  Fed. Rep. of Germany .

OTHER PUBLICATIONS

Wagner and Zook, "Synthetic Organic Chemistry", pp. 801–806 (1953).
Swern, Chemical Reviews, vol. 45, pp. 33–35 (1949).

Primary Examiner—Howard T. Mars
Assistant Examiner—L. Hendriksen
Attorney, Agent, or Firm—William R. Moran

[57] ABSTRACT

An improved process for preparing an organic sulfone compound by oxidizing the corresponding sulfide compound with an aqueous peracid solution.

33 Claims, No Drawings

PREPARATION OF ORGANIC SULFONE COMPOUNDS

BACKGROUND OF THE INVENTION

This invention relates to a process for preparing organic sulfone compounds. More particularly, this invention relates to an improved process for oxidising organic sulfide compounds in a relatively simple and efficient manner to the corresponding organic sulfone compound.

Organic sulfone compounds, as well as oxidation processes for their preparation, are well known in the art. Heretofore, organic sulfone compounds generally have been prepared by one of two oxidation processes which employ a peracid as the oxidising agent. One process, the so called "generator process", involves separately generating an anhydrous peracid oxidizing agent on site to be used for the oxidation of the organic sulfide compound at some later time. The other process, the so called "in-situ" process is a one-step process which calls for the generation of the peracid oxidising agent in-situ in the presence of the organic sulfide compound sought to be oxidized. Although they are relatively simple and efficient, both known processes suffer from a number of inherent disadvantages. For example, it is generally recognized that both of the previously disclosed peracid oxidation processes usually give rise to organic sulfone compounds that are contaminated with an acceptably large amount of the corresponding sulfoxide compound as a by-product. This makes it necessary to carry out elaborate and cumbersome purification procedures which result in relatively low yields of the sulfone product. In addition, the generator process suffers from a further disadvantage in that it requires the generation and handling of the unstable and potentially hazardous anhydrous peracid. The conventional "in-situ" process, although simple and safe to operate, generally requires expensive high boiling reaction solvents, extended reaction periods, and high reaction temperatures with the concomitant increased probability of thermal degradation of reaction products. Consequently, there exists a need for a more effective process for converting organic sulfide compounds in organic sulfone compounds with enhanced sulfone yields coupled with lower reaction temperatures and shorter reaction periods.

SUMMARY OF THE INVENTION

According to the present invention there is provided an improved process for preparing organic sulfone compounds which comprises treating the corresponding sulfide compound with an aqueous peracid solution.

It has been found that the oxidising agent employed in the process of this invention not only provides excellent conversion activity under mild reaction conditions but at the same time exhibits superior selectivity in the oxidation of the sulfide linkage to the exclusion of other oxidizable moieties that may be present in the molecule. The process of this invention is extremely valuable in that it provides a high yield of a high quality organic sulfone compound which is relatively free of sulfoxide contaminants and other reaction by products, while at the same time employing mild reaction conditions, short reaction periods and low reaction temperatures.

DESCRIPTION OF THE PREFERRED EMBODIMENTS

The organic sulfide compounds that can be employed as reactants in the process of this invention include cyclic or linear, aliphatic or aromatic organic compounds containing one or more divalent sulfur functional units. Suitable organic sulfide compounds will contain carbon and hydrogen with oxygen and nitrogen as optional components. The carbon atoms can be acyclic or cyclic; saturated and/or unsaturated such as aliphatic, cycloaliphatic, bicycloaliphatic, aromatic (including fused and bridged carbon atoms and the like). The nitrogen components may be in the form of imino; amino; nitrilo; or nitro groups and the like. The oxygen containing components can be groups such as hydroxyl, either aliphatic or phenolic; carboxyl; carbonyloxy; ether oxy; carbonyl groups or the like. The organic sulfide compound may be substituted with one or more substituents such as chlorine, fluorine, bromine, iodine and the like, the only requirement being that the substituent be unreactive with the peracid unless multiple oxidations are desired.

Preferred organic sulfide reactants are those of the formula:

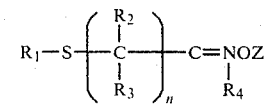

wherein:
n is 0 to 5;
$R_1$ is alkyl, phenyl, phenylalkyl, alkenyl, alkynyl, cycloalkyl or cycloalkenyl all of which may be substituted with one or more chloro, fluoro, bromo, cyano, nitro, alkyl, alkoxy, alkylthio, alkylsulfinyl, alkylsulfonyl or alkoxyalkyl substituents;
$R_2$ and $R_3$ are individually hydrogen or either substituted or unsubstituted alkyl wherein the permissible substituents are one or more chloro, fluoro, bromo, cyano, nitro or alkoxy substituents;
$R_4$ is hydrogen, chloro, fluoro, bromo, cyano, alkyl, alkylsulfonyl, alkoxy, alkylthio, alkylsulfinyl, alkoxy, carboalkoxyalkylsulfonyl, alkoxyalkyl, alkylthioalkyl, alkylsulfonylalkyl or alkylsulfinylalkyl in which any alkyl moiety may be substituted with one or more chloro, bromo, fluoro, cyano, amido or nitro substituents;
Z is hydrogen or

wherein:
$R_5$ and $R_6$ are individually hydrogen or either substituted or unsubstituted alkyl, phenyl or phenylalkyl wherein the permissible substituents are one or more chloro, fluoro, bromo, nitro, cyano, alkyl or alkoxy substituents.

Illustrative of suitable organic sulfide reactants are:
2-Acetylamino-4-methyl-4-nitro-5-thiazolylphenyl sulfide
4-Aminodiphenylsulfide
Benzylcarboxymethyl sulfide
1,2-Bis(2-benzoxyethylmercapto)ethane 1,2-Bis(2-hydroxyethylmercapto)ethane
Bis(4-nitro-1-naphthyl)sulfide
2-Bromo-8-nitrothiaxanthene
Isobutyl 2-chloroethyl sulfide
n-Butyl p-tolyl sulfide
4'-Chloro-4-aminodiphenyl sulfide
2-Chloroethyl p-tolyl sulfide
2-Chloro-2'-methylthiodiethyl sulfide
1-Chlorovinyl 2-chloroethyl sulfide
2-Crotonyl-4'-nitro-5-thiazolphenyl sulfide
2-Ethylthiopropionaldehyde N-methylcarbamoyloxime
2-Phenylthiopropionaldehyde N-methylcarbamoyloxime
2-(a-Naphthylthio)propionaldehyde N-methylcarbamoyloxime
2-Benzylthiopropionaldehyde N-methylcarbamoyloxime
2-(4-Chlorophenylthio)propionaldehyde N-methylcarbamoyloxime
2-(2,4-Dichlorophenylthio)propionaldehyde N-methylcarbamoyloxime
2-Methyl-2-methylthiopropionaldehyde N-methylcarbamoyloxime
2-Methyl-2-ethylthiopropionaldehyde N-methylcarbamoyloxime
2-Methyl-2-n-propylthiopropionaldehyde N-methylcarbamoyl-oxime
2-Methyl-2-isopropylthiopropionaldehyde N-methylcarbamoyl-oxime
2-Methyl-2-butylthiopropionaldehyde N-methylcarbamoyl-oxime
2-Methyl-2-heptylthiopropionaldehyde N-methylcarbamoyl-oxime
2-Methyl-2-decylthiopropionaldehyde N-methylcarbamoyl-oxime
2-Methyl-2-vinylthiopropionaldehyde N-methylcarbamoyl-oxime
2-Methyl-2-(2-propenylthio)propionaldehyde N-methylcarbamoyloxime
2-Methyl-2-(3-butenylthio)propionaldehyde N-methylcarbamoyloxime
2-Methyl-2-hexenylthiopropionaldehyde N-methylcarbamoyloxime
2-Methyl-2-ethynylthiopropionaldehyde N-methylcarbamoyloxime
2-Methyl-2-phenylthiopropionaldehyde N-methylcarbamoyloxime
2-Methyl-2-(a-naphthylthio)propionaldehyde N-methylcarbamoyloxime
2-Methyl-2-benzylthiopropionaldehyde N-methylcarbamoyloxime
2-Methyl-2-(2-chlorophenylthio)propionaldehyde N-methylcarbamoyloxime
Diphenylmethyl a-naphthyl sulfide
Diphenylmethyl phenyl sulfide
Di(p-tolyl) sulfide
Divinyl sulfide
Ethyl n-butyl sulfide
Ethyl ethoxymethyl sulfide
Ethylene-sulfur chloride reaction product
Ethyl oleyl sulfide
4-(2-Hydroxyethylthio)-2-aminobutylric acid
2-Hydroxyethyl naphthenyl sulfides
4-Iodo-4'-nitrodiphenyl sulfide
6-Methoxy-8-(4-quinazolonyl)phenyl sulfide
Allyl benzyl sulfide
2-Methylthiopropionaldehyde N-methylcarbamoyloxime
2-Ethylthiopropionaldehyde N-methylcarbamoyloxime
2-n-Propylthiopropionaldehyde N-methylcarbamoyloxime
2-Isopropylthiopropionaldehyde N-methylcarbamoyloxime
2-n-Butylthiopropionaldehyde N-methylcarbamoyloxime
2-Sec-Butylthiopropionaldehyde N-methylcarbamoyloxime
2-t-Butylthiopropionaldehyde N-methylcarbamoyloxime
2-Isobutylthiopropionaldehyde N-methylcarbamoyloxime
2-heptylthiopropionaldehyde N-methylcarbamoyloxime
2-Decylthiopropionaldehyde N-methylcarbamoyloxime
2-Vinylthiopropionaldehyde N-methylcarbamoyloxime
2-(2-Propenylthio)propionaldehyde N-methylcarbamoyloxime
2-(3-Butenylthio)propionaldehyde N-methylcarbamoyloxime
2-Hexenylthiopropionaldehyde N-methylcarbamoyloxime
2-Methyl-2-(4-chlorophenylthio)propionaldehyde N-methylcarbamoyloxime
2-Methyl-2-(2,4-dichlorophenylthio)propionaldehyde N-methylcarbamoyloxime
2-Methylthiobutylaldehyde N-methylcarbamoyloxime
2-Methylthiopentanaldehyde N-methylcarbamoyloxime
2-Methylthiohexanaldehyde N-methylcarbamoyloxime
2-Methylthioheptanaldehyde N-methylcarbamoyloxime
2-Methylthiodecanaldehyde N-methylcarbamoyloxime
2-Methyl-2-methylthiobutylaldehyde N-methylcarbamoyloxime
2-Ethyl-2-methylthioheptanaldehyde N-methylcarbamoyloxime
2-Butyl-2-methylthioheptanaldehyde N-methylcarbamoyloxime
2-Octyl-2-methylthiodecanaldehyde N-methylcarbamoyloxime
2-[O-(Methylcarbamoyl)oximino]-3,3-dialkyl-1,4-dithiane
3-[O-(Methylcarbamoyl)oximino]-2,2-dialkylthiolane
2-(Ethylthiomethyl)phenyl methylcarbamate
2,4,5-Trichlorophenyl 4-chlorophenyl sulfide
4-(Chlorophenyl)phenyl sulfide
3,5-Dimethyl-4-(methylthio-phenyl methylcarbamate
Bis[4-(methylcarbamoyloxy)phenyl] sulfide
2-Methyl-3-(phenylcarbamoyl)-5,6-dihydro-1,4-oxathin
3-(O-(Methylcarbamoyl-Oximino-2,2-dialkylthiane The oxidising agent utilized in the conduct of the process of this invention is an aqueous peracid solution. Useful peracids components are well known to those skilled in the art. Illustrative of useful peracids are peracetic acid, performic acid, perpropionic acid, pertrifluoroacetic acid, perhexanoic, perpentanoic and the like. In general, the oxidative process of this invention can be effectuated when employing as little as 2 mole of peracid per equivalent of sulfide functional unit present in the sulfide reaction. However to achieve a quantitative conversion of the sulfide compound to the corresponding sulfone compound a molar excess of the peracid is employed. The preferred amount of peracid employed in the conduct of the process of this invention is from about 1.5 moles to about 6 moles of peracid per equivalent of sulfide functional unit. The particularly preferred amount of peracid used is from about 2.2 moles to about 3 moles per equivalent of sulfide functional unit.

The aqueous peracid solution preferably may contain from about 95 to about 50 weight percent water based on the total weight of the aqueous peracid solution. Weight percents outside of this stated range, though not excluded from the scope of the invention, do not fall within the preferred embodiments of this invention. At lower weigh percents the rate of conversion to the desired product becomes markedly slower, due to the reduced peracid concentration, while at the upper weight percent and beyond, signs of peracid instability becomes manifest. The particularly preferred amount of water is from about 55 to about 80 weight percent based on the total weight of the aqueous peracid solution.

Aqueous peracid solutions utilized as oxidising agents in the process of this invention can be generated by reacting the corresponding carboxylic acid with aqueous hydrogen peroxide in the presence of an appropriate catalyst, as disclosed in British Pat. No. 949,094. For example, aqueous peracetic acid solution can be conveniently prepared by charging an equimolar mixture of aqueous hydrogen peroxide and acetic acid into a reaction vessel containing a mixture of acetic acid, hydrogen peroxide and a molar excess of sulfuric acid. The large concentration of sulfuric acid serves both as a catalyst for the reaction and as a dehydration agent to force the reaction equilibrum toward peracetic acid. A large excess of hydrogen peroxide in the reaction vessels also tends to force the reaction toward completion. The reaction vessel is operated at a temperature of from about 50° C. to about 60° C. under a pressure of approximately 60 mm. Hg. Under these reaction conditions the peracetic acid formed in vaporized as its water azeotrope which can be condensed and collected in a conventional condensation system. The concentration of peracetic acid in the aqueous peracid product can be regulated within a wide range by feeding more or less water into the reactor.

The reaction temperature is not critical and can be varied over a wide range. The process is normally conducted at a temperature in the range of from about 0° C. and upwards to approximately 120° C. Preferred reaction temperatures are from about 25° C. to about 75° C. At temperatures below 25° C. the rate of reaction becomes markedly slower, while at temperatures above 75° C. product degradation may occur.

The process can be carried out neat or in solution. A normally liquid organic solvent is preferably employed as the reaction medium. In general any organic solvent inert to oxidation by mild oxidative agents may be used. Illustrative of the organic solvents which are suitable as reaction solvents in the practice of the preferred embodiments of this invention are saturated and unsaturated aliphatic and aromatic hydrocarbons, e.g. hexane, cyclohexane, octane, dodecane, naphtha, decalin, kerosene, tetrahydronapthalene, cycloheptane, alkylcycloalkane, benzene, toluene, xylene, naphthalene, alkylnapthalene, or the like; ethers such as tetrahydrofuran, tetrahydropyran, diethyl ether, dioxane, 1,2-dimethoxybenzene, 1,2-ethoxybenzene, the mono and dialkyl ethers of ethylene glycol, of dipropylene glycol, of butylene glycol, of diethylene glycol, of dipropylene glycol. Preferred solvents for the conduct of the process of this invention are chlorinated aliphatic hydrocarbons as for example, chloroform, methylene dichloride, 1,1-dichloroethane, carbon tetrachloride or the like.

Reaction pressures are not critical. The process of this invention can be conducted at either subatmospheric, atmospheric or superatmospheric pressure. For convenience, the reaction is usually conducted at atmospheric or autogeneous pressure.

The process of this invention is effected over a period of time sufficient to produce the desired organic sulfone compound. In general, residence times can vary from a few minutes to approximately 24 hours or longer. In most instances, when employing preferred reaction conditions, reaction times will be found to vary from about 2 hours to about 4 hours. Reaction time is influenced to a significant degree by the reaction temperature, the concentration and choice of peracid oxidising agent the choice and concentration of diluent and other factors known to those skilled in the synthetic art.

The process of this invention can be conducted in a batch, semicontinuous or continuous fashion. The reaction can be conducted in a single reaction zone or in a plurality of reaction zones, in series or in parallel or it may be conducted intermittently or continuously in an elongated tubular zone or series of such zones. The materials of construction employed should be inert to the reactants during the reaction and the fabrication of the equipment should be able to withstand the reaction temperatures and pressure.

The process is preferably conducted in either glass lined, stainless steel 316 or Hastelloy C-276 reaction equipment. The reaction zone can be fitted with one or more internal and/or external heat exchanger(s) in order to control undue temperature fluctuations, or to prevent any possible "runaway" reaction temperatures. In preferred embodiments of the process, agitation means to vary the degree of mixing the reactions mixture can be employed. Mixing by vibration, shaking, stirring, rotation, oscillation, ultrasonic vibration or the like are all illustrative of the types of agitation means contemplated. Such means are available and well known to those skilled in the art.

The aqueous peracid oxidising agent may be initially introduced into the reaction zone batchwise or it may be continuously or intermittently introduced into such zone during the course of the process. Means to introduce and/or adjust the quantity of reactants introduced, either intermittently or continuously into the reaction zone during the course of the reaction, can be conveniently utilized in the process especially to maintain the desired molar ratio of the solvent and reactants.

In accordance with the preferred embodiments of the process of this invention, an organic sulfide compound is treated with an aqueous peracid solution in a suitable reaction solvent. The manner and order in which the reactants are mixed is not critical. In general, the organic sulfide reactant and a suitable reaction solvent are charged into a suitable reaction vessel, and the aqueous peracid solution is added dropwise, preferably with moderate agitation and the reaction mass heated to the desired temperature.

The manner of practicing the process of the present invention is illustrated by the following specific examples:

EXAMPLE I

Batch Procedure

Procedure: 348 grams (1.63 moles) of a 35.0% aqueous peracetic acid was added dropwise to a mixture containing 140 g (0.74 moles) of 2-Methyl-2-(methylthio)propionaldehyde O-(methylcarbamoyl)oxime in 326 g of methylene chloride. The addition was carried out over a 2 hour period at 40°–41° C. When the addition was complete, the mixture was stirred at 40°–41° C. for an additional hour. The reaction mixture was then stripped at 40°–45° C. until 253 grams of the solvent mixture was removed. The mixture was then cooled to 0° C. and filtered. The solid obtained was washed with 100 ml of chilled water and dried to give 142 g. (86% yield) of 2-Methyl-2-(Methylsulfonyl)propionaldehyde O-(Methylcarbamoyl)oxime (Sulfone) m.p. 137°–139° C.

The mother liquor upon evaporation under reduced pressure, yielded an additional 7.0 g of the sulfone. The total amount of solid obtained was 149 g representing a 90 percent yield of Sulfone, based on the amount of Oxime used. The combined product was found to contain less than 0.10 percent of 2-Methyl-2-(methylsulfinyl)propionaldehyde O-(Methylcarbamoyl)oxime (Sulfoxide) by-product.

EXAMPLE II

Continuous Procedure

Apparatus: The apparatus consisted of 500 ml four-necked flask equipped with a thermometer, stirrer, adapter with two drip-tip tubes, and a dry-ice condenser. The two drip-tip tubes were connected to separate pumps which regulated the feedrates of the solution and the aqueous peracetic acid solution. The reactor was also equipped with a side-arm overflow tubing through which the reaction product could be drained as desired, into a receiver. The reaction temperature in the reactor was maintained at 40°–41° C. by a warm temperature bath.

Procedure: The 2-Methyl-2-(methylthio)propionaldehyde O-(methylcarbamoyl)oxime solution (29–30% in methylene chloride) and 35% aqueous peracetic acid solution were introduced into the reactor at rates of 45 ml/hr. and 56 ml/hr., respectively. After about 2 hours, the accumulated reaction product was allowed to overflow into the receiver kept at −5° C. through the side-drain at 15 minute intervals to maintain a constant volume in the reactor. The process was continued in this manner for about 6 hours. The sulfone product in the receiver was then filtered, washed with water, and dried to constant weight. Under these conditions the continuous operation led to a 90% yield of 2-Methyl-2-(methylsulfonyl)propionaldehyde O-(methylcarbamoyl)oxime (Sulfone) containing less than 0.10 percent of 2-Methyl-2-(methylsulfinyl)propionaldehyde O-(Methylcarbamoyl)oxime (Sulfoxide) by-product.

EXAMPLE III

Procedure: 68 grams of 40% aqueous peracetic acid was added dropwise to a mixture containing 30 grams of phenyl sulfide in 70 grams of methylene chloride. The addition was carried out over a two-hour period at 40°–41° C. After the addition was complete, the mixture was refluxed for an additional two hours. After cooling the organic layer was separated by decantation and washed with water. The washed organic phase was evaporated to dryness under reduced pressure to give approximately 35 g. (100% yield) of phenyl sulfone (Sulfone), which was identified by spectral analyses and melting point. The sulfone product contained less than 0.10 percent of phenyl sulfoxide (Sulfoxide) by-product.

EXAMPLE IV

Procedure: Employing the same reaction conditions as described in Example III, 3,3-dimethyl-1-(methylthio)-2-butanone O-(methylcarbamoyl)oxime was oxidized with a 40% aqueous peracetic acid solution to give 11.2 grams (97.5% yield) of 3,3-dimethyl-1-(methylsulfonyl)-2-butanone O-(methylcarbamoyl)oxime (Sulfone). The resulting product which was identified by spectral analyses as 3,3-dimethyl-1-(methylsulfonyl)-2-butanone O-(methylcarbamoyl)oxime (Sulfone) contained less than 0.10 percent of 3,3-dimethyl-1-(methylsulfinyl)-2-butanone O-(methylcarbamoyl)oxime (Sulfoxide) by-product.

To more particularly demonstrate the increased efficiency of the peracid oxidation process of this invention in comparison with known peracid oxidation processes, the experimental results of three representative examples of the process of this invention were compared with the experimental results from an example of a known process. The comparison data is set forth in TABLE I below. The known peracid oxidation process was conducted as described in EXAMPLE V below.

EXAMPLE V

Procedure: Anhydrous peracetic acid solution (25% peracetic acid in ethyl acetate, 408.4 g., 1.34 moles) was added dropwise to a mixture containing 109 g. (0.57 moles) of 2-Methyl-2-(methylthio)propionaldehyde O-(methyl carbamoyl)oxime in 241 g of acetone over several hours while maintaining the temperature at 25°–35° C. When the addition was complete, the mixture was stirred at 25° C. for an additional 8-hour period. The reaction mixture was then cooled to 5° C. and filtered. The crude reaction product was re-slurried with 330 g of a cold mixture containing 160 g. of methanol, 160 g. of ethyl acetate, and about 10 g. of acetaldehyde. The crude sulfone was then separated by filtration to give 101 g. of wet solid which was found to contain 2.8 weight percent of the sulfoxide as the major contaminant. The crude product was then recrystallized from methanol to give 64 g. (63% yield) of 2-Methyl-2-(methylsulfonyl)propionaldehyde O-(methylcarbamoyl)oxime (Sulfone). The refined sulfone was found to have a 2-Methyl-2-(methylsulfinyl)propionaldehyde O-(methylcarbamoyl)oxime(Sulfoxide) content of 0.4% weight percent.

TABLE I

| | COMPARISON DATA | | | |
| --- | --- | --- | --- | --- |
| | Peracid Solution | | Percent Yield | Sulfoxide |
| Example | % Peracetic | % Water | Of Sulfone | Content |
| I | 35 | 65 | 90 | Less than 0.10% |
| II | 35 | 65 | 90 | Less than 0.10% |
| III | 40 | 60 | 100 | Less than 0.10% |
| IV | 40 | 60 | 97.5 | Less than 0.10% |
| V | 25 | 0 | 63 | 0.47% |

The date presented in TABLE I above clearly illustrates the greatly increased efficiency of the peracid oxidation process of this invention in comparison with known peracid oxidation processes. For example, the known process of EXAMPLE V which was conducted under anhydrous conditions had a 63% yield of the organic sulfone product which contaminated with 0.47% sulfoxide by-product. This result is to be contrasted with EXAMPLES I, II, III and IV which employ the process of this invention. Note that the sulfone product of EXAMPLES I, II, III and IV was produced in an 90, 90, 100 percent and 97.5% yield, respectively. Further EXAMPLES I, IV and V which were conducted under aqueous conditions yielded an organic sulfone product which was contaminated with less than 0.10% of the sulfoxide by-product. This represents a significant increase in the % yield of the sulfone compound and over a 4 fold decrease in the degree of sulfoxide by-product contamination.

The organic sulfone compounds prepared in accordance with the process of this invention have wide utility and are valuable for a number of useful purposes. Some of the organic sulfone compound prepared in accordance with the process of the inventions exhibited outstanding insecticidal, nematocidal and miticidal activity and may be utilized as insecticides, miticides and nematocides according to methods known to those skilled in the pesticidal art. These compounds are also relatively non-toxic to plants and mammals when used in amounts sufficient to kill insects, mites and nematodes. Thus, for example, 2-methyl-2-(methylsulfonyl)-propionaldehyde O-(methylcarbamoyl)oxime an outstanding pesticide may be conveniently prepared by the process of this invention. It should be pointed out, however, that other organic sulfone compounds prepared by the process of this invention are not limited to use as pesticides, but in addition are extremely useful for other purposes which are known to those skilled in the art.

Various modifications and variations of this invention will be obvious to a worker skilled in the art and it is to be understood that such modifications are to be included within the purview of this application and the spirit and scope of the appended claims.

What is claimed is:

1. In a process for preparing an organic sulfone by treating the corresponding sulfide compound with a peracid; the improvement which comprises conducting said process in the presence of from about 50 to about 95 weight percent water based on the total weight of water and peracid.

2. A process according to claim 1 wherein said process is conducted in the presence of from about 55 to about 75 weight percent water based on the total weight of water and peracid.

3. A process according to claim 1 wherein said peracid is selected from the group consisting of performic acid, peracetic acid, perpropionoic acid, perhexanoic acid, or perpentanoic acid.

4. A process according to claim 1 wherein said peracid is selected from the group consisting of performic or peracetic acid.

5. A process according to claim 1 wherein the concentration of said peracid is from about 2 to about 4 moles of peracid per equivalent of sulfide functional unit present in the sulfide reactant.

6. A process according to claim 1 wherein the concentration of said peracid is from about 2.2 to about 3 moles of peracid per equivalent of sulfide functional unit present in the sulfide reactant.

7. A process according to claim 1 which is conducted at a temperature of from about 0° to about 120° C.

8. A process according to claim 1 which is conducted at a temperature of from about 25° to about 75° C.

9. A process for preparing a compound of the formula:

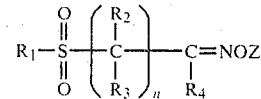

which comprises treating a compound of the formula:

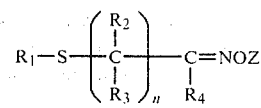

with an aqueous peracid solution, wherein:

n is 0 to 10;

$R_1$ is alkyl, phenyl, phenylalkyl, alkenyl, alkynyl, cycloalkyl or cycloalkenyl all of which may be substituted with one or more chloro, fluoro, bromo, cyano, nitro, alkyl, alkoxy, alkylsulfonyl or alkoxyalkyl groups;

$R_2$ and $R_3$ are individually hydrogen or either substituted or unsubstituted alkyl wherein the permissible substituents are one or more chloro, fluoro, bromo, cyano, nitro or alkoxy groups;

$R_4$ is hydrogen, chloro, fluoro, bromo, cyano, alkyl, alkylsulfonyl, alkoxy, carbalkoxyalkylsulfonyl, alkoxyalkyl or alkylsulfonylalkyl groups in which any alkyl moiety may be substituted with one or more chloro, bromo, fluoro, cyano, amido or nitro group;

Z is hydrogen or

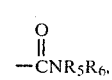

wherein:

$R_5$ and $R_6$ are individually hydrogen or either substituted or unsubstituted alkyl, phenyl or phenylalkyl wherein the permissible substituents are one or more chloro, fluoro, bromo, nitro, cyano, alkyl or alkoxy groups.

10. A process according to claim 9 wherein $R_1$ is alkyl.

11. A process according to claim 9 wherein n is 0, 1 or 2.

12. A process according to claim 9 wherein $R_2$ and $R_3$ are individually hydrogen or alkyl having from 1 to 4 carbon atoms.

13. A process according to claim 9 wherein $R_4$ is hydrogen or alkyl having from 1 to 4 carbon atoms.

14. A process according to claim 9 wherein Z is hydrogen.

15. A process according to claim 9 wherein Z is

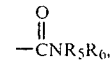

wherein:

$R_5$ and $R_6$ are individually hydrogen or alkyl.

16. A process according to claim 9 wherein said aqueous peracid solution includes from about 50 to about 95 weight percent water based on the total weight of the aqueous peracid solution.

17. A process according to claim 9 wherein said aqueous peracid solution includes from about 55 to about 75 weight percent water based on the total weight of the aqueous peracid solution.

18. A process according to claim 9 wherein said peracid is selected from the group consisting of performic or peracetic acid.

19. A process according to claim 9 wherein the concentration of said peracid is from about 2 to 4 moles of peracid per equivalent of sulfide functional unit present in the sulfide reactant.

20. A process according to claim 9 wherein the concentration of said peracid is from about 2.2 to 3 moles of peracid per equivalent of sulfide function unit present in the sulfide reactant.

21. A process according to claim 9 which is conducted at a temperature of from about 0° to about 120° C.

22. A process according to claim 9 which is conducted at a temperature of from about 25° C. to about 75° C.

23. A process for preparing a compound of the formula:

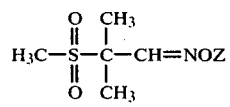

which comprises treating a compound of the formula:

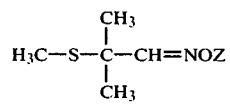

with an aqueous peracid solution, wherein:
Z is hydrogen or

24. A process according to claim 23 wherein said aqueous peracid solution includes from about 50 to about 95 weight percent water based on the total weight of the aqueous peracid solution.

25. A process according to claim 23 wherein said aqueous peracid solution includes from about 55 to about 75 weight percent water based on the total weight of the aqueous peracid solution.

26. A process according to claim 23 wherein said peracid is selected from the group consisting of performic acid, peracetic acid, perpropionic acid, perhexanoic acid or perpentanoic acid.

27. A process according to claim 23 wherein said peracid is selected from the group consisting of performic or peracetic acid.

28. A process according to claim 23 wherein the concentration of said peracid is from about 2 to about 4 moles of peracid per equivalent of sulfide functional unit.

29. A process according to claim 23 wherein the concentration of said peracid is from about 2.2 to about 3 moles of peracid per equivalent of sulfide functional unit present in the sulfide reactant.

30. A process according to claim 23 which is conducted at a temperature in the range of from about 0° C. to about 120° C.

31. A process according to claim 23 which is conducted at a temperature in the range of from about 25° C. to about 75° C.

32. A process for preparing a compound of the formula:

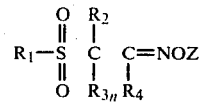

by reacting a compound of the formula:

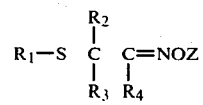

wherein:
n is 0 to 10;
$R_1$ is alkyl, phenyl, phenylalkyl, alkenyl, alkynyl, cycloalkyl or cycloalkenyl all of which may be unsubstituted or substituted with one or more chloro, fluoro, bromo, cyano, nitro, alkyl, alkoxy, alkylsulfonyl or alkoxyalkyl groups;
$R_2$ and $R_3$ are individually hydrogen or either substituted or unsubstituted alkyl wherein the permissible substituents are one or more chloro, fluoro, bromo, cyano, nitro or alkoxy groups;
$R_4$ is hydrogen, chloro, fluoro, bromo, cyano, alkyl, alkylsulfonyl, alkoxy, carboalkoxyalkylsulfonyl, alkoxyalkyl or alkylsulfonylalkyl, groups in which any alkyl moiety may be substituted with one or more chloro, bromo, fluoro, cyano, amido or nitro group;
Z is hydrogen or

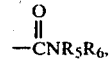

wherein
$R_5$ and $R_6$ are individually hydrogen or either substituted or unsubstituted alkyl, phenyl or phenylalkyl wherein the permissible substituents are one or more chloro, fluoro, bromo, nitro, cyano, alkyl or alkoxy groups; with a peracid in the presence of from 50 to about 95 weight percent water based on the total weight of water and peracid.

33. A process according to claim 32, wherein said peracid is selected from the group consisting of performic acid, peracetic acid, perpropionic acid, perbutanoic acid, perpentanoic acid and perhexanoic acid.

* * * * *

UNITED STATES PATENT AND TRADEMARK OFFICE
CERTIFICATE OF CORRECTION

PATENT NO. : 4,248,795

DATED : February 3, 1981

INVENTOR(S) : John Kai-Fai Chan

It is certified that error appears in the above—identified patent and that said Letters Patent is hereby corrected as shown below:

Title page, under Inventor, "John K. Chan" should read, -- John Kai-Fai Chan --.

Column 5, line 11, "weigh" should read -- weight --.

Column 5, line 36, "in" should read -- is --.

Column 12, claim 32, the formula in first instance, $$" R_1-\underset{O}{\overset{O}{\underset{\|}{\overset{\|}{S}}}}\quad \underset{R_{3n}}{\overset{R_2}{C}}\quad \underset{R_4}{C}=NOZ \text{ "}, \text{ should read}$$

$$-- \quad R_1-\underset{O}{\overset{O}{\underset{\|}{\overset{\|}{S}}}}-\underset{R_{3n}}{\overset{R_2}{C}}-\underset{R_4}{C}=NOZ \quad --.$$

UNITED STATES PATENT AND TRADEMARK OFFICE
CERTIFICATE OF CORRECTION

PATENT NO. : 4,248,795

DATED : February 3, 1981

INVENTOR(S) : John Kai-Fai Chan

It is certified that error appears in the above—identified patent and that said Letters Patent is hereby corrected as shown below:

Column 12, claim 32, the formula in second instance, $$\text{"} \quad R_1 - S \quad \overset{R_2}{\underset{R_3}{C}} \quad \overset{}{\underset{R_4}{C}} = NOZ \quad \text{"}, \text{ should read}$$

$$-- \quad R_1 - S - \overset{R_2}{\underset{R_3}{C}} - \overset{}{\underset{R_4}{C}} = NOZ \quad --.$$

Signed and Sealed this

Twenty-third Day of June 1981

[SEAL]

Attest:

RENE D. TEGTMEYER

*Attesting Officer*  *Acting Commissioner of Patents and Trademarks*

UNITED STATES PATENT AND TRADEMARK OFFICE
CERTIFICATE OF CORRECTION

PATENT NO. : 4,248,795
DATED : February 3, 1981
INVENTOR(S) : John Kai-Fai Chan

It is certified that error appears in the above—identified patent and that said Letters Patent is hereby corrected as shown below:

Column 2, line 55, the formula

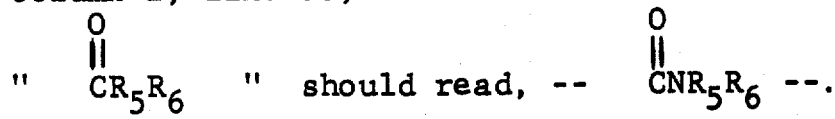

Column 12, claim 32, the formula in first instance,

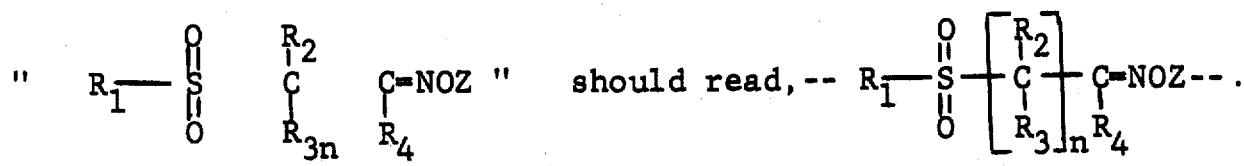

Column 12, claim 32, the formula in second instance,

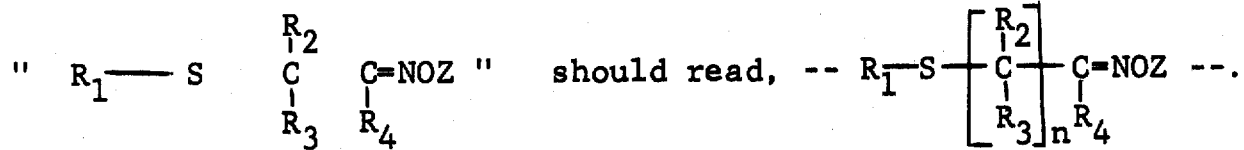

Signed and Sealed this

Eighth Day of September 1981

[SEAL]

Attest:

Attesting Officer

GERALD J. MOSSINGHOFF

Commissioner of Patents and Trademarks